United States Patent [19]
Shafer et al.

[11] Patent Number: 5,756,801
[45] Date of Patent: May 26, 1998

[54] METHOD OF PURIFYING DIPHENYL CARBONATE-PHENOL ADDUCT

[75] Inventors: Sheldon Jay Shafer, Clifton Park; Eric James Pressman, East Greenbush, both of N.Y.

[73] Assignee: General Electric Company, Schenectady, N.Y.

[21] Appl. No.: 797,068

[22] Filed: Feb. 10, 1997

[51] Int. Cl.$^6$ .................................................. C07C 68/08
[52] U.S. Cl. ........................... 558/274; 558/270; 558/271; 558/272; 558/273
[58] Field of Search .............................................. 558/274

[56] References Cited

U.S. PATENT DOCUMENTS 5,239,106   8/1993   Shafer.
5,312,955   5/1994   Pressman et al..

Primary Examiner—Michael G. Ambrose
Attorney, Agent, or Firm—William H. Pittman

[57] ABSTRACT

Adducts of hydroxyaromatic compounds such as phenol and diaryl carbonates such as diphenyl carbonate are washed with a washing composition comprising a major proportion, typically about 90%, of the hydroxyaromatic compound and a minor proportion, typically about 10%, of the diaryl carbonate.

4 Claims, No Drawings

METHOD OF PURIFYING DIPHENYL CARBONATE-PHENOL ADDUCT

BACKGROUND OF THE INVENTION

This invention relates to the preparation of diaryl carbonates, and more particularly to their preparation by a method which comprises isolation and purification of a solid diaryl carbonate adduct.

Diaryl carbonates, especially diphenyl carbonate, are valuable intermediates for the preparation of polycarbonates by reaction in the melt in a transesterification reaction with dihydroxyaromatic compounds, particularly with 2,2-bis(4-hydroxyphenyl)propane or "bisphenol A". This method of polycarbonate preparation is environmentally advantageous by reason of its avoidance of the use of pollutants and toxic materials such as methylene chloride and phosgene.

The diaryl carbonates employed in the transesterification method may be prepared by the reaction of a hydroxyaromatic compound such as phenol with carbon monoxide and oxygen in the presence of a catalyst. Typical catalysts are mixtures of a palladium compound; an inorganic co-catalyst which may be a cobalt complex; an organic co-catalyst such as a terpyridine; and a source of chloride or bromide, preferably bromide, such as a tetraalkylammonium bromide or hexaalkylguanidinium bromide. The resulting reaction mixture is typically a mixture of diaryl carbonate, hydroxyaromatic compound and catalyst constituents or reaction products. It is, of course, necessary to separate the diaryl carbonate from the other constituents of the mixture.

A separation method which is frequently advantageous is described in U.S. Pat. Nos. 5,239,106 and 5,312,955. It includes a step of forming, at a temperature up to about 50° C. and preferably in the range of about 25°–50° C., a solid adduct of hydroxyaromatic compound and diaryl carbonate, typically having a stoichiometry approximating 1:1 molar. This adduct can be conveniently separated from the reaction mixture and subsequently thermally cracked, at temperatures in the range of about 40°–180° C. and under reduced pressure. Such cracking results in removal of the hydroxyaromatic compound by volatilization and the recovery of diaryl carbonate of high purity.

Isolation of the adduct in the above-described procedure is normally by filtration. Any filtration operation, however, will leave some quantity of residual mother liquor on the isolated product crystals. In the case of the adduct, the mother liquor will be predominately phenol but will include substantial proportions of catalyst constituents and other impurities, including by-products of the carbonylation reaction.

Thus, it is conventional to wash solid products separated by filtration. The aforementioned U.S. Pat. No. 5,239,106 briefly alludes to the use of "aqueous phenol", also known as "liquefied phenol", which is a mixture of phenol with a minor proportion of water, for this purpose.

The choice of an optimum washing liquid for the adduct is, however, problematic in view of the diverse requirements thereof. The washing liquid must selectively dissolve and remove mother liquor and impurities without dissolving a major proportion of the adduct. Further, it should not add chemicals foreign to the process which might contaminate the final product, the diaryl carbonate. Thus, liquefied phenol as described hereinabove is less than ideal by reason of the introduction of water, which is foreign to the process.

SUMMARY OF THE INVENTION

The present invention affords a high purity adduct of dihydroxyaromatic compound and diaryl carbonate. This adduct is prepared by a method which includes a step of washing the adduct crystals within a specific temperature range and with a material having the aforementioned properties.

The invention is a method for purifying a crystalline adduct of a hydroxyaromatic compound and a diaryl carbonate corresponding to said hydroxyaromatic compound which comprises washing said adduct, at a temperature up to about 35° C., with a washing composition comprising a major proportion of said hydroxyaromatic compound and a minor proportion of said diary carbonate, said washing composition being liquid at said temperature.

DETAILED DESCRIPTION OF THE PREFERRED EMBODIMENTS

The present invention may be employed for the purification of any crystalline adduct of a hydroxyaromatic compound and a diaryl carbonate corresponding to said hydroxyaromatic compound. The preferred adduct is usually of phenol and diphenyl carbonate, by reason of the relatively low cost and particular suitability of diphenyl carbonate as an intermediate for polycarbonate preparation. Thus, frequent reference hereinafter will be made to these reagents, but it should be understood that other hydroxyaromatic compounds and the corresponding diaryl carbonates may be substituted therefor as appropriate. While the stoichiometry of the adduct is not critical, any crystalline adduct which is formed being suitable, it is generally found that the adduct obtained is or approximates 1:1 molar.

For the most part, the adduct is the reaction product of phenol, carbon monoxide and oxygen and is formed by a reaction which takes place in the presence of a catalyst mixture such as that described hereinabove. An excess of phenol is ordinarily present during said reaction, whereupon diphenyl carbonate can form the adduct by contact with said excess at a temperature up to about 50° C. Thus, while the carbonylation reaction may be conducted at higher temperatures, the adduct forms and precipitates upon cooling the reaction mixture.

Separation of the adduct from the reaction mixture is conveniently effected by filtration, especially vacuum filtration, which yields the adduct as a solid product contaminated with mother liquor which ordinarily contains some quantity of catalyst constituents or the reaction products thereof, as well as reaction by-products. According to the present invention, such extraneous materials are removed by washing the adduct, at a temperature up to about 35° C., with a washing composition comprising a major proportion of phenol.

Since substantially pure phenol has a melting point on the order of 41° C., it cannot be used as a washing composition. If it were, the required washing temperature approaching 45° C. would result in substantial amounts of the adduct being melted and/or dissolved, with a concomitant loss of diphenyl carbonate.

According to the present invention, therefore, the washing composition comprises a minor proportion of diphenyl carbonate. Any phenol-diphenyl carbonate mixture having a melting point of 35° C. or below may be employed. The preferred washing compositions contain diphenyl carbonate in proportions up to about 10% by weight.

The washing operation may comprise merely contacting the filtered adduct with the washing composition at a temperature up to about 35° C. Washing temperatures in the range of about 20°–30° C. are frequently preferred by reason of the decreased degree of dissolution of the adduct in the washing composition at such lower temperatures.

Following washing, the procedures in the aforementioned U.S. Pat. Nos. 5,239,106 and 5,312,955 may be performed to crack the adduct into its constituents, and the diphenyl carbonate may be recovered therefrom. Cracking is, as previously mentioned, typically effected by heating the adduct to a temperature in the range of about 40°–180° C. under reduced pressure. Such heating results in volatilization of the phenol, whereupon the product diphenyl carbonate may be recovered and employed for polycarbonate formation.

The method of this invention is illustrated by an example in which a stirred crystallization vessel maintained at 35° C. was charged with 262.9 parts by weight of a synthetic reaction mixture consisting of 54.7% (by weight) phenol, 39.6% diphenyl carbonate, 500 ppm of palladium as palladium acetate and 248 ppm of cobalt as the pentacoordinate complex with bis[3,3'-(salicylal)aminopropyl]methylamine. Upon stirring the mixture for several hours, the diphenyl carbonate-phenol adduct crystallized.

The mixture was filtered on a Buchner funnel maintained at 35° C., and a 1.1-part sample of the crystallized adduct which collected of the filter was removed for analysis. The remaining adduct was washed with 49.1 part of a liquid mixture of 10% (by weight) diphenyl carbonate and 90% phenol. Upon analysis, the various product streams and components were found to have the compositions listed in the following table.

| Source | Phenol, % | Diphenyl carbonate, % | Pd, ppm. | Co, ppm. |
|---|---|---|---|---|
| Original reaction mixture | 54.7 | 39.6 | 500 | 248 |
| Adduct mother liquor | 70.9 | 21.8 | 659 | 362 |
| Crude adduct (solid) | 40.3 | 59.8 | 132 | 84 |
| Adduct washing liquid | 76.3 | 20.3 | 239 | 130 |
| Washed adduct (solid) | 38.7 | 61.8 | <10 | 16 |

The results in the table demonstrate that the highest proportion of diphenyl carbonate was found in the washed adduct. It is also apparent that even in crude form, the adduct contains relatively low proportions of palladium and cobalt; however, these proportions are materially decreased by washing.

What is claimed is:

1. A method for purifying a crystalline adduct of a hydroxyaromatic compound and a diaryl carbonate corresponding to said hydroxyaromatic compound which comprises washing said adduct, at a temperature up to about 35° C., with a washing composition comprising a major proportion of said hydroxyaromatic compound and a minor proportion of said diaryl carbonate, said washing composition being liquid at said temperature.

2. A method according to claim 1 wherein the hydroxyaromatic compound is phenol and the diaryl carbonate is diphenyl carbonate.

3. A method according to claim 2 wherein the washing composition comprises about 10% by weight diphenyl carbonate, with the balance being phenol.

4. A method according to claim 2 wherein the temperature is in the range of about 20°–30° C.

* * * * *